United States Patent
Pawliszyn et al.

(10) Patent No.: US 6,852,206 B2
(45) Date of Patent: Feb. 8, 2005

(54) MEASUREMENT OF FLUORESCENCE USING CAPILLARY ISOELECTRIC FOCUSING

(75) Inventors: Janusz Pawliszyn, 383 Dunvegan Drive, Waterloo, Ontario (CA), N2K 1W7; Xing-Zheng Wu, Fukui (JP); Tiemin Huang, Waterloo (CA)

(73) Assignee: Janusz Pawliszyn, Waterloo (CA)

( * ) Notice: Subject to any disclaimer, the term of this patent is extended or adjusted under 35 U.S.C. 154(b) by 644 days.

(21) Appl. No.: 09/832,807

(22) Filed: Apr. 12, 2001

(65) Prior Publication Data

US 2001/0054554 A1 Dec. 27, 2001

Related U.S. Application Data

(60) Provisional application No. 60/196,588, filed on Apr. 13, 2000.

(51) Int. Cl.$^7$ ................................................. C02F 1/469
(52) U.S. Cl. ....................... 204/610; 204/601; 204/603; 204/612
(58) Field of Search ................................ 204/610, 601, 204/603, 612

(56) References Cited

U.S. PATENT DOCUMENTS 5,324,401 A * 6/1994 Yeung et al. ............... 204/452

OTHER PUBLICATIONS

Huang et al., "Axially illuminated fluorescene imaging detection for capillary isoelectric focusing on Teflon capillary", The Analy Communication, 125, 1231–1233(2000).*

Johansson, "Fluorescene imaging of light absorption for axially–beam geomtry in capillary electrophorescene", Electrophoresis 19, 2233–2238(1998).*

Taylor et al., "Axial–beam laser–excited fluorescence detection in capillary electrophoresis", Anal. Chem., 64, 1741–1744(1992).*

* cited by examiner

*Primary Examiner*—Ling-Siu Choi
(74) *Attorney, Agent, or Firm*—Ridout & Maybee LLP

(57) ABSTRACT

Improved apparatus is disclosed for carrying out axially illuminated laser induced fluorescence whole-column imaging detection in the capillary isoelectric focusing of proteins. The separation capillary was made of low refractive index Teflon conditioned with methylcellulose to reduce electroosmotic flow and a small amount of high refractive index organic solvent (glycerol) was added to the sample mixture. It was found that an axially directed laser excitation beam was propagated essentially with total internal reflection, so that minimum interference arose from stray light or from scattering light originating from the wall of the capillary. With the naturally fluorescent protein R-phycoerythrin, a concentration detection limit LOD $10^{-11}$ M or mass LOD $10^{-17}$ Mo was obtained.

7 Claims, 4 Drawing Sheets

MEASUREMENT OF FLUORESCENCE USING CAPILLARY ISOELECTRIC FOCUSING

This application claims the benefit of Provisional Application No. 60/196,588, filed Apr. 13, 2000.

BACKGROUND OF THE INVENTION

This invention relates to the detection of analytes separated from a mixture by capillary isoelectric focusing (CIEF) using axially illuminated laser induced fluorescence (LIF) and whole-column imaging detection (WCID) of fluorescence emitted by the analytes.

BRIEF REVIEW OF THE PRIOR ART

The publications referred to in what follows and identified by footnotes are incorporated by reference herein for their teachings as to capillary electrophoretic techniques.

Capillary electrophoresis (CE) has been established as an important separation method in bioanalytical chemistry. Separation and detection of very small amounts of biological samples, about pL-nL volumes, can be achieved with CE. This is generally not possible with more conventional separatory methods, even high performance liquid chromatography (HPLC). There are several CE separation methods in use for different kinds of samples. They include capillary zone electrophoresis, moving boundary capillary electrophoresis, capillary isotachophoresis and capillary isoelectric focusing.

Isoelectric focusing (IEF) is a special electrophoretic technique for separating amphoteric substances such as peptides and proteins in an electric field, across which there is both a voltage and a pH gradient, acidic in the region of the anode and alkaline near the cathode. Each substance in the mixture will migrate to a position in the separation column where the surrounding pH corresponds to its isoelectric point. There, in zwitterion form with no net charge, molecules of that substance cease to move in the electric field. Different amphoteric substances are thereby focused into narrow stationary bands.

Capillary isoelectric focusing, CIEF is a high resolution capillary electrophoresis technique for the separation of proteins and other zwitterionic biomolecules [1,2]. It has most often been used to separate closely related proteins with subtle differences in their structures.

In conventional "single point on-column" detection CIEF, the focused zone within the capillary must be moved, chemically or electroosmotically, past a detection point to be detected. This mobilization step in CIEF requires extra time and distorts the focused zone, thus making it difficult to obtain reproducible qualitative and quantitative results.

To eliminate the mobilization step in single-point detection CIEF, "whole column imaging detection", WCID of CIEF has been explored in the past decade. Wu and Pawliszyn demonstrated a concentration gradient imaging system in 1992 [3]. A photodiode driven by a microsyringe pump was used to measure the light intensity, and the focusing process in 3 cm of a 5 cm separation capillary could be monitored. This on-line detector greatly reduced the analysis time of CIEF from around 20 minutes to less than 5 minutes.

An off-line whole column detector was demonstrated by Wang and Hartwick in the same year [4]. After CIEF focusing, the separation capillary was transferred to a scanning detector, and pulled by a synchronous motor to conduct whole column detection. Because the capillary in the system also functions as a lens, any small change in the position of the capillary results in a large shift in the light path through the cylindrical capillary, causing high dynamic noise.

A spatial-scanning laser fluorescence detection of CE was reported by Beale [5], in which a laser-induced fluorescence (LIF) detector uses epi-illumination to scan the entire separation capillary. The capillary was mounted on a Plexiglas stage on a table, which was driven by a servomotor. The fluorescence signal from the moving capillary was collected by a photo-multiplier tube (PMT) and a low concentration detection limit of $10^{-9}$ M for fluorescein isothiocyanate (FITC)-myoglobin was obtained.

WCID techniques developed by Wu and Pawliszyn have been applied to UV absorption [6,7], to concentration gradient [8], and to LIF [9] using a CCD camera. UV WCID has been successfully commercialized [10,11]. As the lower end detection limit of UV WCID is normally relatively high (usually 10 $\mu$g/mL for protein), a more sensitive WCID method is needed for broader application of WCID CIEF.

LIF would appear to recommend itself as the basis for the desired WCID method of enhanced sensitivity, as LIF provides the lowest detection limit in CE. As few as a hundred molecules can be detected [12]. However, the application of LIF to CIEF presents difficult problems of alignment of the source of excitation light with the small internal diameter capillary and the collection of emission fluorescence.

In particular, the radiation of the sample-containing capillary in a direction perpendicular to the capillary axis gives only a very short excitation path and gives rise to the difficulty of interference by light scattered from the wall of the capillary. To minimize the interference of scattered light and to increase the path link of the incident exciting radiation, axial illumination LIF has been explored for CE.

Johansson and Nilsson demonstrated fluorescence imaging of light absorption for axial-beam geometry in CE [13]. The probing UV light was introduced axially at one end of the fused silica capillary. Excitation light intensity decayed exponentially along the capillary. Based on fluorescence imaging of light absorption along a separation capillary, the loss of fluorescence intensity of sample peaks can be detected by a charge-coupled device (CCD) camera.

However, the method employed by Johansson and Nilsson's "single-point detection" (as opposed to WCID) requires a special buffer including a high refractive index organic solvent, dimethyl sulfoxide. Moreover, their method is not adaptable for whole column imaging detection.

Taylor and Yeung reported an axial-beam laser excited fluorescence in CE [14] which also employed a single point detection method. Total internal reflection of incident light inside the capillary was realized by using a high refractive index solvent dimethyl sulfoxide (DMSO) in a fused silica capillary. An LOD of $6 \times 10^{-12}$ M of rhodamine 6G was estimated.

It is an object of the present invention to provide capillary electrophoresis apparatus using a capillary made of a material which greatly reduces loss of light through the capillary wall, and permits whole-column imaging detection to be carried out of greater sensitivity than known CIEF procedures using "single-point" detection of analyte fluorescence.

SUMMARY OF THE INVENTION

With a view to overcoming the aforementioned disadvantages of prior methods for fluorescence detection in capillary electrophoresis and affording sensitive detection of ampholytes such as protein, the present invention provides apparatus for axially illuminated laser induced fluorescence whole-column imaging detection for capillary isoelectric focusing, in which the exciting laser beam is introduced directly into the separation capillary by a piece of optical fibre mounted axially into the separation capillary.

The capillary is fabricated of a material of sufficiently low refractive index to effect internal reflection of axially induced exciting irradiation. Suitable low-refractive index materials include Teflon™. A fused silicate capillary thinly coated inside with such low refractive index materials can also be used in the invention. If a small amount of high refractive index organic solvent such as glycerol has been added to the sample mixture, the incident laser beam is axially propagated along the interior of the capillary with essentially total internal reflection, so that light scattered from the wall of the capillary is too faint to interfere significantly with the measurement of analyte fluorescence.

Whether the separation capillary is made entirely of a low-refractive index material such as Teflon (PTFE) or is a conventional fused silica capillary which has been interiorly coated by such low-refraction, internally reflecting materials, it is also important that the interior of the separation capillary be coated with a material that does not interact with the analytes of interests, such as proteins. Conventionally, fused silica separation channels used in capillary electrophoresis of proteins are conditioned with methyl cellulose to avoid surface binding and other reactions with protein analytes. Methyl cellulose can be used in the present invention as well, with the thickness of that innermost coating as thin as a single monolayer.

The invention also contemplates use of a multi-channel CIEF device in which the separation column comprises a plurality of such capillaries in a unitary cartridge.

BRIEF DESCRIPTION OF THE DRAWINGS

The invention will now be described further reference to the accompanying drawings, in which.

DETAILED DESCRIPTION OF THE INVENTION

Apparatus

Figure 1:
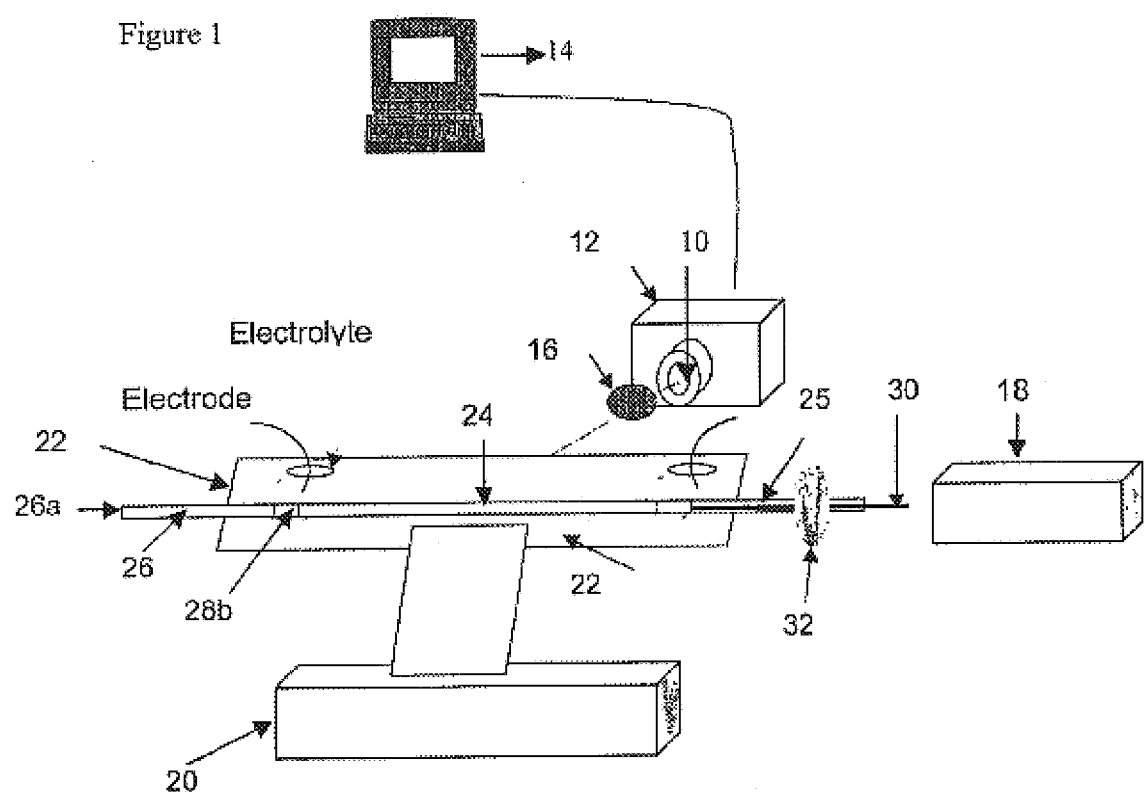
FIG. 1 is a schematic representation of apparatus for axially illuminated, laser-induced fluorescent whole column imaging detection of analytes under CIEF.

A schematic of the axially illuminated LIF WCID is shown in FIG. 1. In the system, a small UV lens 10 (A4869, Hamamatsu Inc, Japan) was coupled to an UV-sensitive CCD camera 12, which was controlled by a ST-130 controller (TEA/CCD-1752/PF/UV, 14, Princeton Instrument, Trenton, N.J. USA). An edge filter 16 (LL-550-s-577 D, Corion, Mass., USA) was placed in front of the camera. The camera 12 was thermoelectrically cooled down to −40° C. and all the parameters were adjusted to get a clear image. The electropherogram was obtained by binning perpendicular to the capillary axis to get a better signal to noise ratio.

The power supply (not illustrated) was a RE-3002B (Regulated High-voltage supply, Mass). An air-cooled argon ion laser 18 (Cyonics, CA) was used as the excitation source. An x-y translatable stage 20 was used to facilitate adjusting the capillary cartridge to let the laser light pass axially through the capillary.

A cartridge 22 carrying separation capillary 24 is also shown in FIG. 1. A glass plate 26 was used as support for capillaries of the cartridge. The polyfluorocarbon separation capillary 24 was a 6 cm long PTFE (Teflon) or FEP (fluorinated ethylene propylene copolymer) capillary. The end of capillary 24 facing the source of light is connected to a second piece 25 of like capillary tubing, and the other end 24b is connected to a piece of 100 µm i.d. UV-transparent fused silica capillary 26 by small pieces of microporous hollow fiber 28a and 28b. Suitable to such sections of hollow fiber may be pieces of commercially available dialysis hollow fibers (Spectrum Medical Industries, Inc. Los Angeles, Calif.).

A piece of optical fiber 30 was inserted into the end of capillary 24 to facilitate introduction of the laser beam, axially into the medium in the lumen of the capillary.

The sample was injected from the fused silica capillary end 26a. Interference produced by stray light and scattering light was avoided by using screen 32 with a central pinhole for holding the laser beam introduction capillary section 25.

Materials And Chemicals

Optical fibers with 100 µm core and 61 µm core (FVP100110125, FHP061067075A) were purchased from Polymicro Technologies Inc (Phoenix Ariz.). Microporous hollow fiber with pore size of 0.03 µm and 383.3 µm ID was obtained form Hoechst Celanese. Polytetrafluoroethylene (PTFE) capillaries of 100 µm ID, 229 µm OD, and fluorinated ethylene propylene (FEP) capillary of 305 µm ID, 620 µm OD were obtained from Zeus (Raritan, N.J.). PTFE capillaries of 102 µm ID., 406 µm OD, 203 µm ID, and 406 µm OD were obtained from Cole-Parmer Instrument Co (Vernon Hills, Ill.).

R-phycoerythrin was purchased from Calbiochem-Novabiochem Corporation (La Jolla, Calif.). Methylcellulose, glycerol, and Pharmalyte of pH 3–10 were obtained from Sigma (St Louse, Mo.) and were of analytical grade.

Water was purified using an ultra-pure water system (Barnstead/Thermolyne, Dubuque, Iowa), and was used for all solutions.

Samples were prepared by mixing spiked protein, carrier ampholytes (CAs) and a desired solvent.

Experimental Results and Discussion

WCID is usually conducted in electro-osmotic flow-controlled fused silica capillary cartridges, in which the focusing process can be monitoring in a real time mode by a CCD camera. However, total internal reflection is difficult to implement in fused silica capillary, because of the high refractive index of fused silica. The CIEF process is a unique CE separation mode in that a high percentage of organic solvent may cause protein precipitation, or make isoelectric focusing impossible.

Teflon and plastic capillaries have been investigated as separation capillaries for CE for their flexibility, durability, stability in basic buffer, and most importantly the low refractive index.

Electro-osmotic flow should be eliminated or minimized in CIEF, and surface modification and sample additive modification are commonly used for this purpose. Ren and Lee reported a method to control EOF in plastic capillary by surface modification of the capillary with cellulose [15,16]. Wu also recommends conditioning fluorocarbon coated capillary with methyl cellulose (MC) solution [10].

We found that if the Teflon separation capillary 24 was not conditioned with MC solution, the EOF was so strong that focusing would not complete. However, it was virtually eliminated in Teflon capillary after conditioning by 0.35% MC for a half hour. EOF was not thereafter observed even with no MC added to the sample mixture itself.

Figure 2:
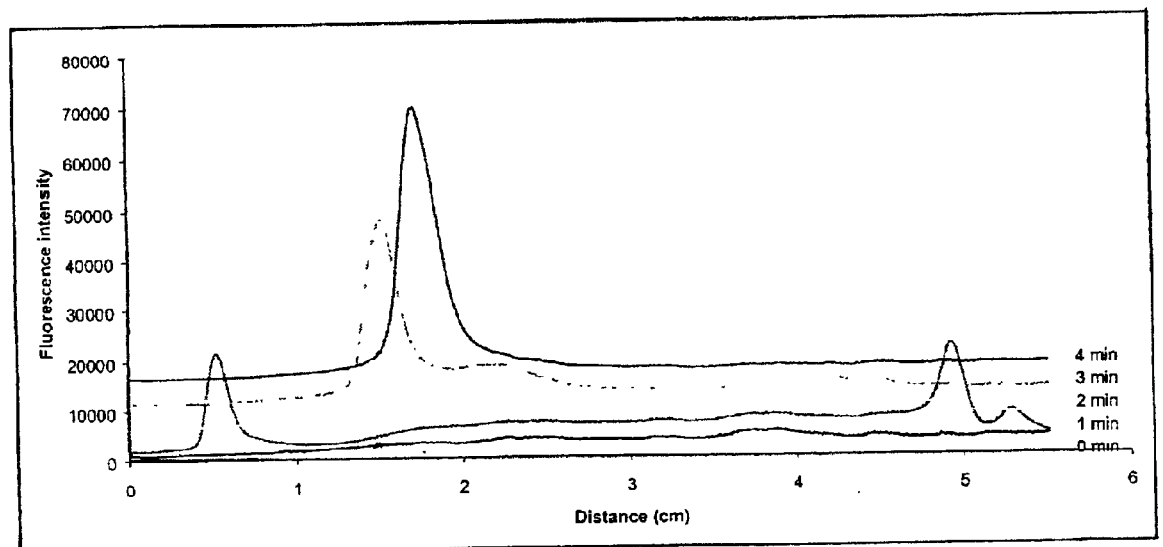
FIG. 2 is a graphical presentation of fluorescence intensity as a function of distance along the capillary, to show dynamic focusing of the fluorescent protein R-phycoerythrin over focusing times of 1 to 4 minutes.

The dynamic focusing of R-phycoerythrin is shown in FIG. 2. The separation capillary was 200 µm ID PTFE. The protein sample concentration was 20 µg/mL ($8.3 \times 10^{-8}$ M), the carrier ampholytes were 2%, and glycerol was 20%. 20 mM of phosphorous acid and 40 mM of sodium hydroxide were used as ampholytes and catholyte respectively. The exposure time of the CCD camera was 10 milliseconds. 3 KV focusing voltage was applied.

As the focusing process and peak position were very reproducible, the isoelectric point (pI) of R-phycoerythrin could be calculated from the peak position in the separation capillary as 5.0. To prevent sample photodegradation, the laser was turned on only during taking the imaging.

This is an important precaution as many kinds of potential analytes will be gradually bleached by laser irradiation. From FIG. 2, it can be seen that the fluorescence intensity was homogeneous across the entire capillary before applying high voltage. Once the laser was turned on, photobleaching was more serious closer to the inlet of laser beam during focusing.

Two naturally fluorescent proteins, R-phycoerythrin and Green Fluorescent Protein (GFP) were separated by the established system. The GFP sample solution was received as a gift from Convergent Bioscience Ltd, and the concentration was 0.5 mg/mL. The proteins were mixed in an aqueous migration medium with 4% pH 3–10 pharmalyte, and 0.35% methyl cellulose. Cartridges of 200 μm ID PTFE were used to separate the naturally fluorescent proteins. The capillaries were conditioned with 0.35% MC for 20 minutes and 3000 V was used to conduct the isoelectric focusing, with exposure time of 250 milliseconds. The maximum emission wavelengths for R-phycoerythrin and GFP are 560 and 515 nm respectively. When no filter was used, the interference light was too strong to observe the fluorescence signal, while only GFP could be detected when using the 515 nm interference filter. Both R-phycoerythrin and GFP could be detected when the edge filter was used, with the sacrifice of the sensitivity of GFP.

Figure 3:
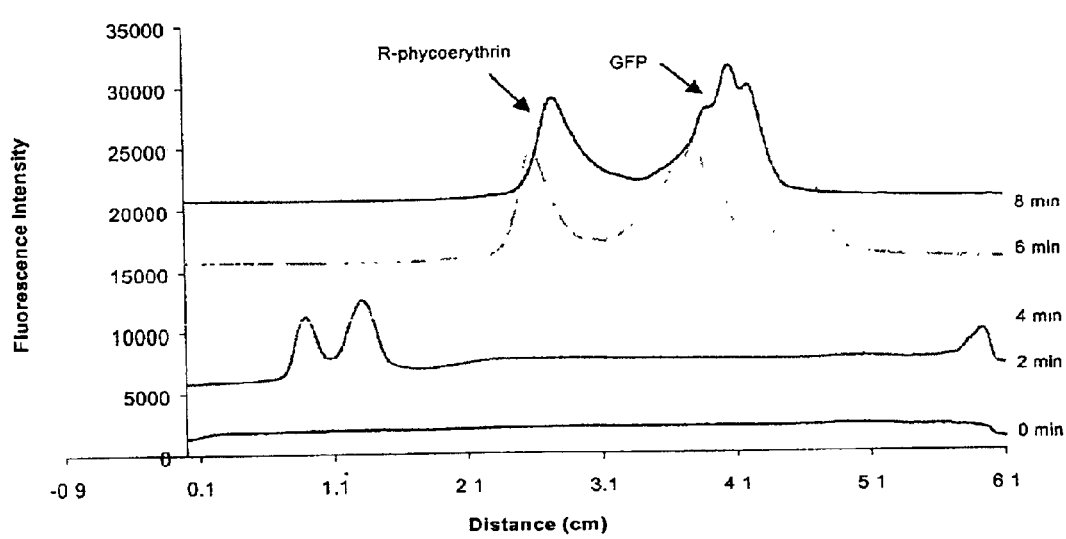
FIG. 3 is a graphical representation of fluorescence intensity versus distance as in FIG. 2, illustrating the dynamic focusing over time of a mixture of R-phycoerythrin and Green Fluorescent Protein (GFP)

FIG. 3 shows the dynamic focusing of the two naturally fluorescent proteins. The separation conditions are the same as in FIG. 2, except the exposure time of the CCD camera was 250 milliseconds. The concentration of R-phycoerythrin and GFP were 8 ppb and 1 ppm respectively.

Direct illumination of the separation capillary by the laser beam was also investigated. The fluorescence intensity did not change significantly, although illumination using an optical fiber produced a better signal to noise ratio (S/N), and less interference. The laser beam was introduced by a piece of optical fiber 30 mounted axially into the separation capillary 24, so most of the scattering light was eliminated in axially illuminated LIF. There was no need to use a filter to produce a narrow band excitation light, and thus stronger incident light was obtained. Because the edge filter could not discriminate the unwanted luminescence coming from the wall of the Teflon capillary, and the scattering light by the submicron particles in the sample mixture, the background interference was significant during longer exposure time. Under these conditions, LOD (S/N=3) of $10^{-11}$ M for R-phycoerythrin was still obtained.

CCD is an ideal imaging detector for LIF. The dark current noise ($N_d$) and the read noise ($N_r$) are very low in a TE cooled CCD camera, thus photo shot noise ($N_s$) is dominant. The total noise ($N_T$) in a CCD detector is defined as [17]:

$$N_T = \sqrt{N_s^2 + N_r^2 + N_d^2} \quad (1)$$

$N_s$ refers to photon arriving randomly at the detector, and is equal to the square root of the number of photogenerated charges;

$N_d$ refers to charge accumulating in the detector when not being exposed to radiation (a few electrons per pixel per second);

$N_r$ refers to the random movement of charge in the device and associated readout electronics (also a few electrons per pixel per second).

Because $N_r(N_r = \sqrt{KTC})$, where k is Boltzmann's constant, T is temperature, and C is capacitance, is independent of the magnitude of the signal, the S/N improves in direct proportion to the signal level. The signal can be increased by longer integration times or by an increase in the incident light intensity, which is easily accomplished in LIF CCD detection.

From the electropherogram, it was also noticed that the peak was much broader than those obtained from UV WCID. This may partly due to the fact that the collected signal in LIF is emission (all direction), while in UV it is absorption (one direction); or due to protein adsorption as protein-capillary surface interaction is more serious in plastic capillary than in modified fused silica capillary. Suitable resolution may be achieved by applying a high electric field, selecting narrow pH gradient carrier ampholytes and a longer separation capillary, as well as by minimizing the protein—capillary surface interaction.

In the course of our experimentation using axially illuminated laser-induced fluorescence to detect proteins separated by isoelectric focusing, we discovered that it was possible to create the pH gradient required for electrophoresis without the addition of carrier ampholytes. This promises significant advantages in that carrier ampholytes are relatively expensive, may undesirably interact with samples and generally are troublesome to eliminate in preparative isoelectric focusing. We determined that proteins can be separated in a capillary which contains pure water by virtue of the pH gradient which is created by the migration of hydrogen and hydroxide ions, with the effects amplified by adding and acidic buffer to the fluid in the reservoir containing the positive electrode (anolyte) and a basic buffer to the fluid in the reservoir containing the negative electrode (catholyte).

Hydronium and hydroxide ions migrate to the capillary, forming a pH gradient with pH=7 at the point where the amounts of hydronium and hydroxide ions are the same. These ions and cations are produced in the usual way by the electrolysis of water.

The anode reaction may be represented by the equation:

$$H_2O - 2H^+ + \frac{1}{2}O_2$$

The analogous cathode reaction may be represented by the equation:

$$H_2O + 2e = 2OH^- + \frac{1}{2}H_2$$

The electromigration of these hydronium and hydroxide ions in the electric field along the length of the separation capillary creates a pH gradient.

Figure 4:
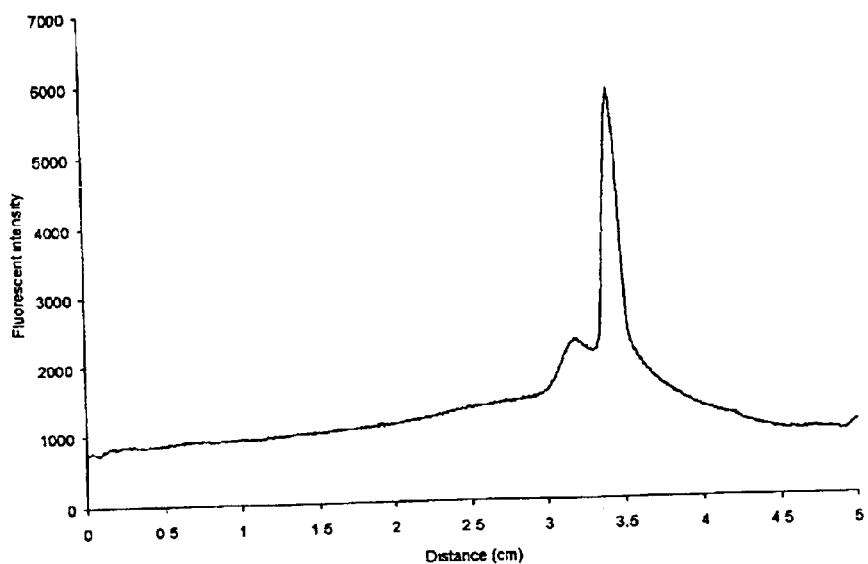
FIGS. 4, 5, 6 and 7 are graphs of fluorescence measurements at differing times of electrophoresis by CIEF, in which the analyte-containing solution in the capillary has no added carrier ampholytes.
Figure 5:
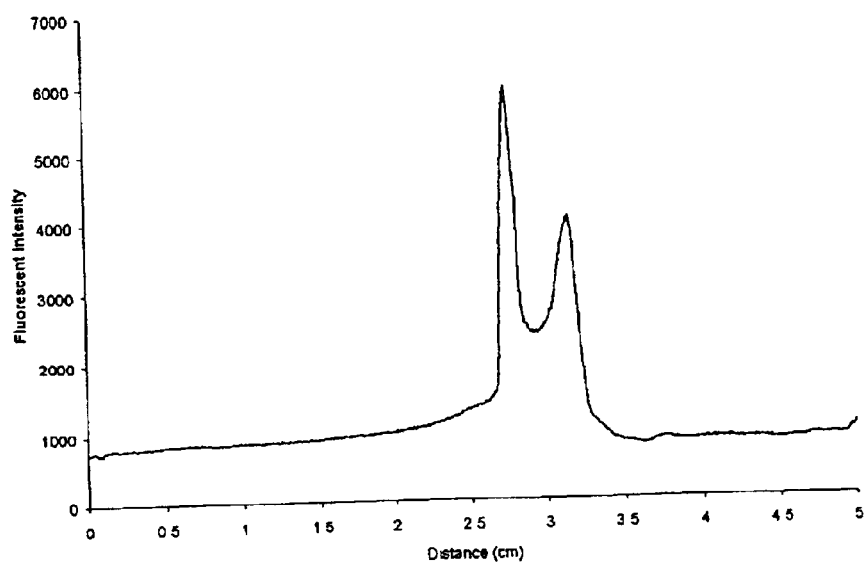
Figure 6:
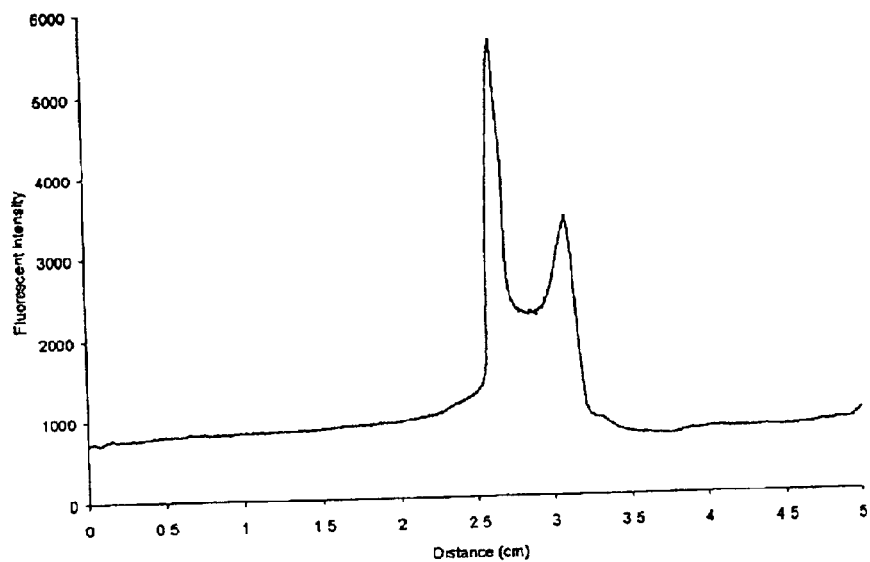

We have successfully separated two naturally fluorescent proteins with pI points close together using CIEF without carrier ampholytes, by means of axially illuminated LIF detection. FIGS. 4, 5 and 6 are graphical presentations of the separation of fluorescence peaks for R-phycoerythrin (3.3× $10^{-10}$ M) and Green Fluorescent Protein (1.8×$10^{-8}$ M). The separation capillary used was 200 μm i.d. PTFE having a length of 5 cm. The samples were directly dissolved in pure water. The anolyte was 100 mM phosphorus acid and the catholyte was 100 mM sodium hydroxide. The voltage applied was 2000V and the earlier-described measurements of whole-column imaging detection was used.

Figure 7:
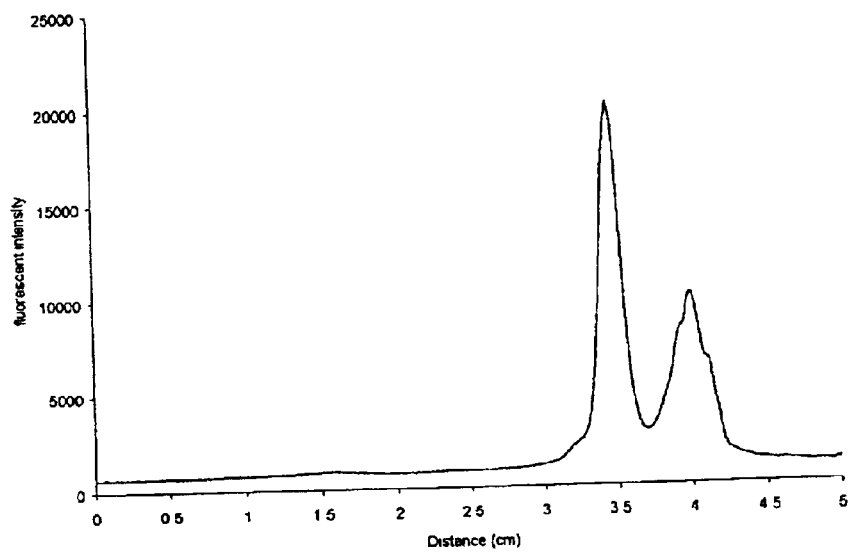

FIGS. 4, 5 and 6 represent the focusing of the R-phycoerythrin (left peak) and the GFP (right peak) at 10 seconds, 50 seconds and 2 minutes respectively. By way of comparison, FIG. 7 shows the focusing of the same concentrations of R-phycoerythrin and Green Fluorescent Protein but at 3000V applied voltage and 4% carrier ampholyte (pH 3–10) added to the capillary tube, all other experimental conditions being same as described in connection with FIGS. 4 to 6.

Other experiments which we carried out, but in which the analyte peaks were determined by UV-absorption showed that two high molecular weight proteins (hemo control and cytochrome C) could be separated without using carrier ampholytes.

Conclusions

An axially illuminated WCID LIF for CIEF was developed. An LOD on the attomole ($10^{-17}$) level for a naturally fluorescence protein R-phycoerythrin was obtained. The developed method will facilitate CIEF trace analysis of protein, and the study of protein-protein interactions such as binding reaction and immunoreaction.

By using a highly sensitive fluorescence tag and coupling with a sample preparation technique like solid phase microextraction (SPME) with on-fibre labeling with derivatization reagent, ultra high sensitivity can be expected, which may be applied in applications such as single cell analysis.

REFERENCES

1. Paitchett J. Thomas *Electrophoresis* 1996, 17, 1195–1201
2. Kuhn R.; Hoffsterrer-Kuhn S. *Capillary Electrophoresis: Principles and Practice*, Springer Laboratory, Berlin Heidelberg, Germany,1993
3. Wu J; Pawliszyn J. *Anal. Chem.* 1992, 64, 224–227
4. Wang T.; Hartwick R. A. *Anal. Chem.* 1992, 64, 1745–1747
5. Beale S. C.; Sudmeier S. J. *Anal. Chem.* 1995, 67, 3367–3371
6. Wu J; Pawliszyn J *Analyst* 1995, 120, 1567–1571
7. Wu J; Pawliszyn J *J. Chromatogr. B* 1994, 657, 327–332
8. Wu J; Pawliszyn J. *Anal. Chem.* 1992, 64, 2934–2941
9. Wu X.; Wu J.; Pawliszyn J. *Electrophoresis* 1995, 16, 1474–1478
10. Wu J; Watson A. *J. Chromatogr. B* 1998, 714, 113–118
11. Wu J; Watson A. *J. Chromatogr. A* 1998, 817, 163–171
12. Craig D. B.; Dovichi N. J. *Anal. Chem.* 1996, 68, 697–700
13. Johansson J.; Johansson T.; Nilsson S. *Electrophoresis* 1998, 19, 2233–2238
14. Taylor J. A.; Yeung E. S. *Anal. Chem.* 1992, 64, 1741–1744

What is claimed is:

1. Apparatus for capillary isoelectric focusing, comprising:

a separation capillary filled with a migration medium in which fluorescent analytes migrate or are in stationary equilibrium;

a laser light source for axial irradiation of said capillary at one end thereof to excite said fluorescent analytes; and whole column imaging detection means for monitoring the isoelectric focusing process, wherein said separation capillary is made of a material having a sufficiently low refractive index that the intensity of laser light scattered from the walls of said separation capillary is negligible relative to the fluorescence of the analytes in the migration medium.

2. Apparatus according to claim 1, wherein said capillary material is a fluorinated polyalkene.

3. Apparatus according to claim 2, wherein said fluorinated polyalkene is selected from the group consisting of polytetrafluoroethylene and fluorinated ethylene-propylene copolymers.

4. Apparatus according to claim 1, wherein said separation capillary is a section of fused silica glass capillary tubing having a interior coating of a low refractive index material.

5. Apparatus according to claim 3, further comprising a section of optical fibre extending into said one end of the separation capillary and outwardly toward and in alignment with said laser light source, for directing irradiating light from the laser axially into the lumen of the capillary.

6. Apparatus according to claim 5, further comprising a screen interposed between said one end of the separation capillary and said light source, having a central pinhole to allow the close passage therethrough of said section of optical fibre.

7. Apparatus according to claim 3, claim 5 or claim 6, wherein said whole column imaging detection means comprises a charge-coupled device camera coupled to an ultraviolet transparent lens.

\* \* \* \* \*